United States Patent
Lee et al.

(10) Patent No.: US 12,266,162 B2
(45) Date of Patent: Apr. 1, 2025

(54) ENHANCING CONTRAST SENSITIVITY AND RESOLUTION IN A GRATING INTERFEROMETER BY MACHINE LEARNING

(71) Applicant: RENSSELAER POLYTECHNIC INSTITUTE, Troy, NY (US)

(72) Inventors: Seung Wook Lee, Busan (KR); Seho Lee, Busan (KR); Ge Wang, Loudonville, NY (US)

(73) Assignee: RENSSELAER POLYTECHNIC INSTITUTE, Troy, NY (US)

( * ) Notice: Subject to any disclaimer, the term of this patent is extended or adjusted under 35 U.S.C. 154(b) by 0 days.

(21) Appl. No.: 17/766,365

(22) PCT Filed: Oct. 8, 2019

(86) PCT No.: PCT/US2019/055189
§ 371 (c)(1),
(2) Date: Apr. 4, 2022

(87) PCT Pub. No.: WO2020/033979
PCT Pub. Date: Feb. 13, 2020

(65) Prior Publication Data
US 2024/0046629 A1    Feb. 8, 2024

Related U.S. Application Data

(60) Provisional application No. 62/910,670, filed on Oct. 4, 2019.

(30) Foreign Application Priority Data

Aug. 8, 2018 (KR) .................. 10-2018-0092483

(51) Int. Cl.
*G06V 10/82* (2022.01)
*G02B 6/293* (2006.01)
*G06V 10/75* (2022.01)

(52) U.S. Cl.
CPC .......... *G06V 10/82* (2022.01); *G02B 6/29353* (2013.01); *G06V 10/751* (2022.01); *G06V 2201/03* (2022.01)

(58) Field of Classification Search
CPC ............ G01B 9/02083; G01B 2290/30; G02B 6/29353; G06V 10/751; G06V 10/82;
(Continued)

(56) References Cited

U.S. PATENT DOCUMENTS

| 5,784,162 A | 7/1998 | Cabib et al. |
| 8,005,185 B2 | 8/2011 | Popescu |

(Continued)

FOREIGN PATENT DOCUMENTS

| CN | 106023107 A | * 10/2016 | ........... G06T 1/0007 |
| CN | 107194376 A | 9/2017 | |

(Continued)

OTHER PUBLICATIONS

International Search Report and The Written Opinion of the International Searching Authority, International Application No. PCT/US2019/055189, mailed Jan. 13, 2020.

(Continued)

*Primary Examiner* — Michael A Lyons
(74) *Attorney, Agent, or Firm* — Barclay Damon, LLP; Anthony P. Gangemi (57) ABSTRACT

The present disclosure relates to an apparatus for enhancing contrast sensitivity and resolution in a grating interferometer by machine learning, which can improve both image contrast sensitivity and spatial resolution in a grating interferometer by machine learning, the apparatus including: an (Continued)

image acquisition unit; a numerical phantom generation unit, a convolution layer generation unit to extract features from input data; an activation function application calculation unit that can apply a rectified linear activation function to an output value of the convolution calculation to perform smooth repetitive machine learning; a CNN repetitive machine learning unit that corrects a convolution calculation factor while repeatedly performing forward propagation and backward propagation processes; and an image matching output unit that matches and outputs features extracted by repetitive machine learning of the CNN repetitive machine learning unit.

9 Claims, 7 Drawing Sheets

(58) Field of Classification Search
CPC ........ G06V 2201/03; G06N 3/02; G06N 3/08; G06N 3/084
See application file for complete search history.

(56) References Cited

U.S. PATENT DOCUMENTS

| | | | |
|---|---|---|---|
| 9,329,141 | B2 | 5/2016 | Stutman et al. |
| 10,172,580 | B2 | 1/2019 | Roessl et al. |
| 10,748,036 | B2 * | 8/2020 | Tu .............................. G06T 7/11 |
| 2012/0265050 | A1 | 10/2012 | Wang |
| 2020/0408929 | A1 * | 12/2020 | Wang ......................... G01T 1/17 |
| 2021/0374936 | A1 * | 12/2021 | Koopman ............. G06V 10/764 |

FOREIGN PATENT DOCUMENTS

| | | | | |
|---|---|---|---|---|
| JP | H06235619 A | | 8/1994 | |
| WO | WO-2019071433 A1 * | | 4/2019 | ........... G06N 3/0454 |

OTHER PUBLICATIONS

Rubeaux, M. et al., "Numerical phantom generation to evaluate non-rigid CT-CBCT registration algorithms for prostate cancer radiotherapy," Proceedings of the first MICCAI workshop on Image-Guidance and Multimodal Dose Planning in Radiation Therapy: 15th International Conference on Medical Image Computing and Computer Assisted Intervention, pp. 74-81, Oct. 2012.

* cited by examiner

ENHANCING CONTRAST SENSITIVITY AND RESOLUTION IN A GRATING INTERFEROMETER BY MACHINE LEARNING

CROSS REFERENCE TO RELATED APPLICATION(S)

This application claims the benefit of Korean Patent Application No. 10-2018-0092483, filed in the Korean Intellectual Property Office Aug. 8, 2018, and U.S. Provisional Application No. 62/910,670, filed Oct. 4, 2019, which are incorporated by reference as if disclosed herein in their entirety.

STATEMENT REGARDING FEDERALLY SPONSORED RESEARCH OR DEVELOPMENT

This invention was made with government support under Grant EB016977, awarded by the National Institutes of Health. The government has certain rights in the invention.

FIELD

The present disclosure relates to a grating interferometer, and more particularly to enhancing contrast sensitivity and resolution in a grating interferometer by machine learning.

BACKGROUND

X-radiation and neutron radiography are widely used for non-destructive testing since X-rays and neutrons can pass through an object without damaging it. X-rays and neutrons react to electrons and atomic nuclei, respectively, and may be attenuated while passing through the object.

In general, a radiographic image used in a non-destructive test corresponds to absorption imaging and shows an absorption contrast sensitivity according to a linear attenuation coefficient of an object.

Radiographic images have been developed through various applications in science. Radiographic imaging includes, but is not limited to, dark-field imaging and phase-contrast imaging using a grating interferometer in which an interference principle is applied to radiation.

SUMMARY

In an embodiment, there is provided an apparatus for enhancing contrast sensitivity and resolution in a grating interferometer by machine learning. The apparatus includes a grating interferometer image acquisition unit, a numerical phantom generation unit, a convolution layer generation unit, an activation function application calculation unit, a CNN (convolutional neural network) repetitive machine learning unit and an image matching output unit. The grating interferometer image acquisition unit is configured to acquire a relatively high-resolution image and a relatively high sensitivity image by linearly moving a position of a sample from the symmetrical grating interferometer. The numerical phantom generation unit is configured to generate a numerical phantom for performing machine learning. The convolution layer generation unit is configured to perform calculation processing of a convolutional neural network to extract features from input data. The activation function application calculation unit is configured to apply a ReLu (Rectified linear unit) activation function to an output value of the convolution calculation to perform smooth repetitive machine learning. The CNN repetitive machine learning unit is configured to correct a convolution calculation factor while repeatedly performing forward propagation and backward propagation processes. The image matching output unit is configured to match and provide as output features extracted by repetitive machine learning of the CNN repetitive machine learning unit.

In some embodiments, the grating interferometer image acquisition unit is configured to acquire a pair of relatively high contrast sensitivity image and relatively high-resolution image by installing a symmetrical grating interferometer and linearly moving the position of the subject and performs an image size rearrangement process to match different magnifications of the respective images.

In some embodiments, the numerical phantom generation unit is configured to measure the resolution, contrast sensitivity and image noise of the acquired phase difference image, implement the same level of images in numerical simulation and generate a plurality of numerical phantoms for relatively high accuracy.

In some embodiments, the convolution layer generation unit is configured to generate a filter which is a convolution calculation factor in order to subject the input data to convolution, has a horizontal and vertical size smaller than the input data and allows the number of filters to be 32 or more.

In some embodiments, the convolution calculation of the input data and the filter in the convolution layer generation unit includes setting zero padding, stride, and the size of the generated filter in order to keep the result of the convolution calculation equal to the horizontal and vertical size of the input image. The size of the output data includes $$(C_o, R_o) = \left( \frac{C_i + 2P - C_f}{S} + 1, \frac{R_i + 2P - R_f}{S} + 1 \right),$$

where $(C_o, R_o)$ is the size of the output data (C=column, R=row), $(C_i, R_i)$ is the size of the input data, S is the stride, P is zero-padding, and $(C_f, R_f)$ is the size of the filter.

In some embodiments, in the convolution calculation of the input data and the filter in the convolution layer generation unit, zero padding is performed to solve the problem that the edge information of the input data disappears, and the result of the convolution calculation adjusts the size of the output data to the same size as the input value by setting the stride to 1 (stride=1) when the filter is moved within the input data.

In some embodiments, the activation function application calculation unit is configured to apply a ReLu function to an output value obtained from the calculation of each convolution layer, thereby reducing an error that may occur during repetitive machine learning performed later.

In some embodiments, in the CNN repetitive machine learning unit, the forward propagation uses the convolutional calculation of the input data generated by the simulation and the convolution calculation factor to finally calculate a loss value of a cost function, and the back propagation corrects weight and bias by partially differentiating the convolution calculation factor in the reverse direction of the forward propagation calculation in order to minimize the loss.

In some embodiments, the CNN repetitive machine learning unit is configured to generate a cost function that reduces the difference between the result value of the convolution calculation performed from the input image and the ground truth, and repeatedly perform forward propagation and backward propagation processes in a direction in which the generated cost function is reduced.

DETAILED DESCRIPTION

The features and advantages of an apparatus, method and/or system for enhancing contrast sensitivity and resolution in a grating interferometer by machine learning according to the present disclosure will be apparent from the detailed description of each embodiment below.

Figure 1:
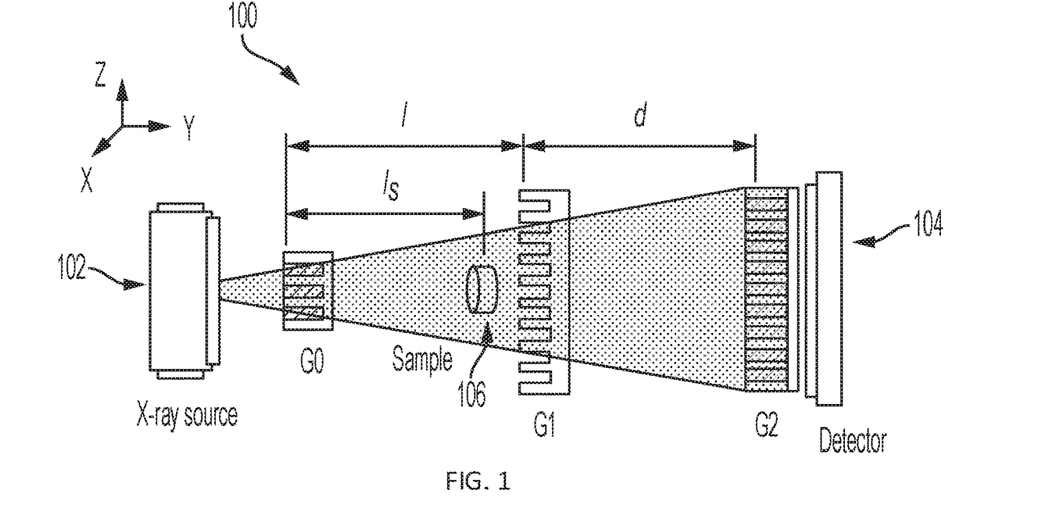
FIG. 1 illustrates one example of an X-ray grating interferometer, consistent with several embodiments of the present disclosure.

FIG. 1 illustrates one example of an X-ray grating interferometer 100, consistent with several embodiments of the present disclosure. The X-ray grating interferometer 100 includes a source grating G0, a phase grating G1, and an absorption grating G2. In one nonlimiting example, the X-ray grating interferometer 100 corresponds to a Talbot-Lau interferometer. The source grating G0 is positioned relatively near an x-ray source 102. The absorption grating G2 is positioned relatively near a detector 104. The phase grating G1 is positioned between the source grating G0 and the absorption grating G2. A sample 106 may be positioned a distance $l_s$ from the source grating G0. As used herein, the terms "sample", "subject" and "object" are used interchangeably to indicate the item being imaged. The phase grating G1 is positioned a distance l from the source grating and the absorption grating G2 is positioned a distance d from the phase grating G1.

The source grating G0 is configured to improve a spatial coherence of X-rays. The X-rays that have passed through the G0 grating may generate interference patterns due to the wave nature of the X-rays while passing through the phase grating G1. For such a pattern, the intensity changes while having a specific period.

When the absorption grating G2 is positioned at a specific distance according to the period and the phase stepping process of the grating is additionally performed, the phase information $\Delta\Phi$ of the sample can be acquired from a general detector. The $\Delta\Phi$ value acquired in this way is more sensitive than the linear attenuation coefficient $\mu$ acquired from a conventional X-ray image, thus improving the contrast between objects.

Acquisition of images having a relatively high contrast (or relatively high sensitivity) in such an X-ray grating interferometer 100 is related to the position of the gratings G0, G1, G2 and the position of the sample 106 relative to the gratings.

Figure 2:
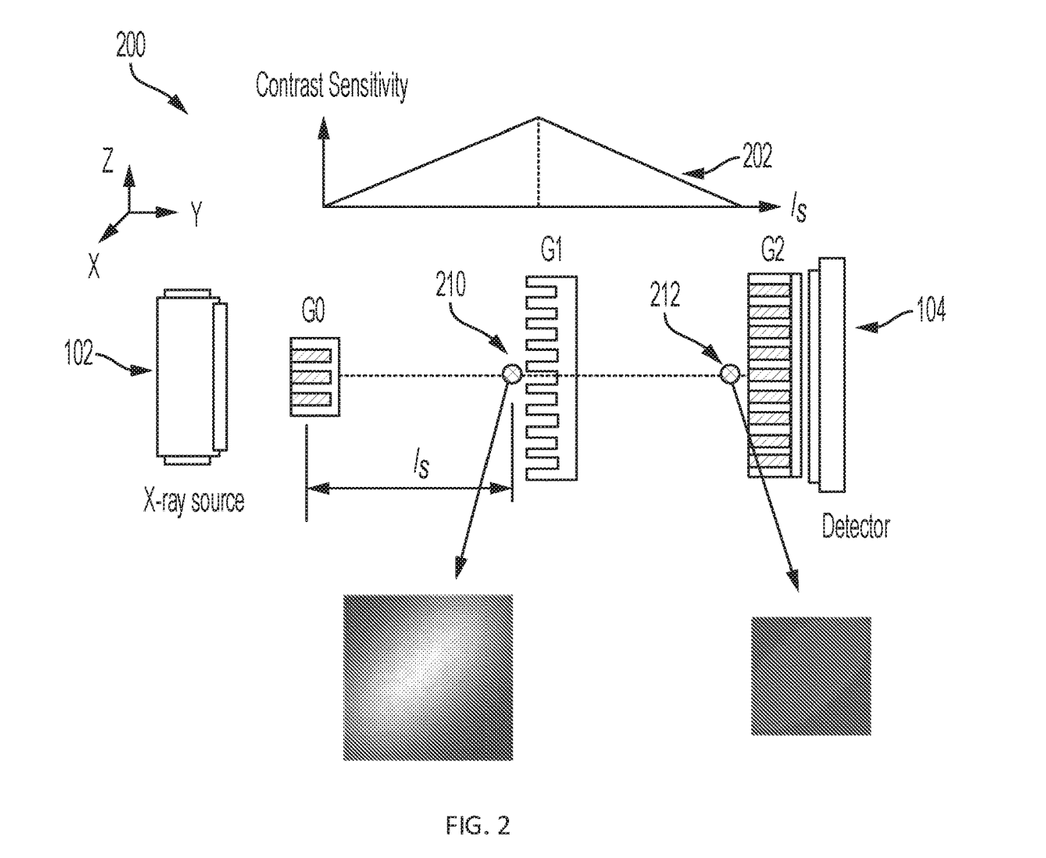
FIG. 2 is an X-ray grating interferometer, illustrating contrast sensitivity versus position of sample relative to gratings.

FIG. 2 is an X-ray grating interferometer 200, illustrating contrast sensitivity versus position 202 of sample relative to gratings. When a sample 210 is positioned immediately before or behind the phase grating G1, images having the highest contrast sensitivity can be acquired, and as the distance of the sample from the phase grating G1 increases, e.g., sample 212, the contrast sensitivity decreases linearly.

The distances l and d may be determined based, at least in part, on the pattern cycle of the grating, the plating depth, the X-ray energy, etc. Thus, the spatial resolution according to the position of a sample may not be considered.

For example, if the sample is positioned closer to the X-ray source 102, magnification may increase but the sharpness decreases. As the sample position moves away from the X-ray source, the magnification decreases but the sharpness increases. These relationships can be used to determine the highest resolution section for the respective systems.

Since the factors for determining the contrast sensitivity of the grating interferometer and the resolution of the X-ray image are independent of each other, a sample position having both a relatively high contrast sensitivity and a relatively high resolution simultaneously may not exist. Thus, it is practically difficult to simultaneously acquire relatively high contrast sensitivity and relatively high resolution of a subject in a grating interferometer.

A method, apparatus and/or system, consistent with the present disclosure may be configured to improve both contrast sensitivity and spatial resolution in a grating interferometer by machine learning. The method, apparatus and/or system may be configured to extract image information with relatively high contrast sensitivity and relatively high resolution from images at various positions of a sample positioned in a grating interferometer system using a convolutional neural network (CNN). The method, apparatus and/or system may be configured to improve the contrast sensitivity and resolution of the phase difference image by using a convolutional neural network and thus provide a relatively high-quality medical image.

The method, apparatus and/or system may be configured to enhance contrast sensitivity and resolution in a grating interferometer by machine learning, making it possible to improve the contrast sensitivity and resolution of the phase difference image using a convolutional neural network, thereby increasing the applicability to other medical imaging systems beyond the X-ray and neutron imaging field, and developing new medical device market.

The objects of the present disclosure are not limited to the above-mentioned objects, and other objects not mentioned will be clearly understood by those skilled in the art from the following description.

Figure 3:
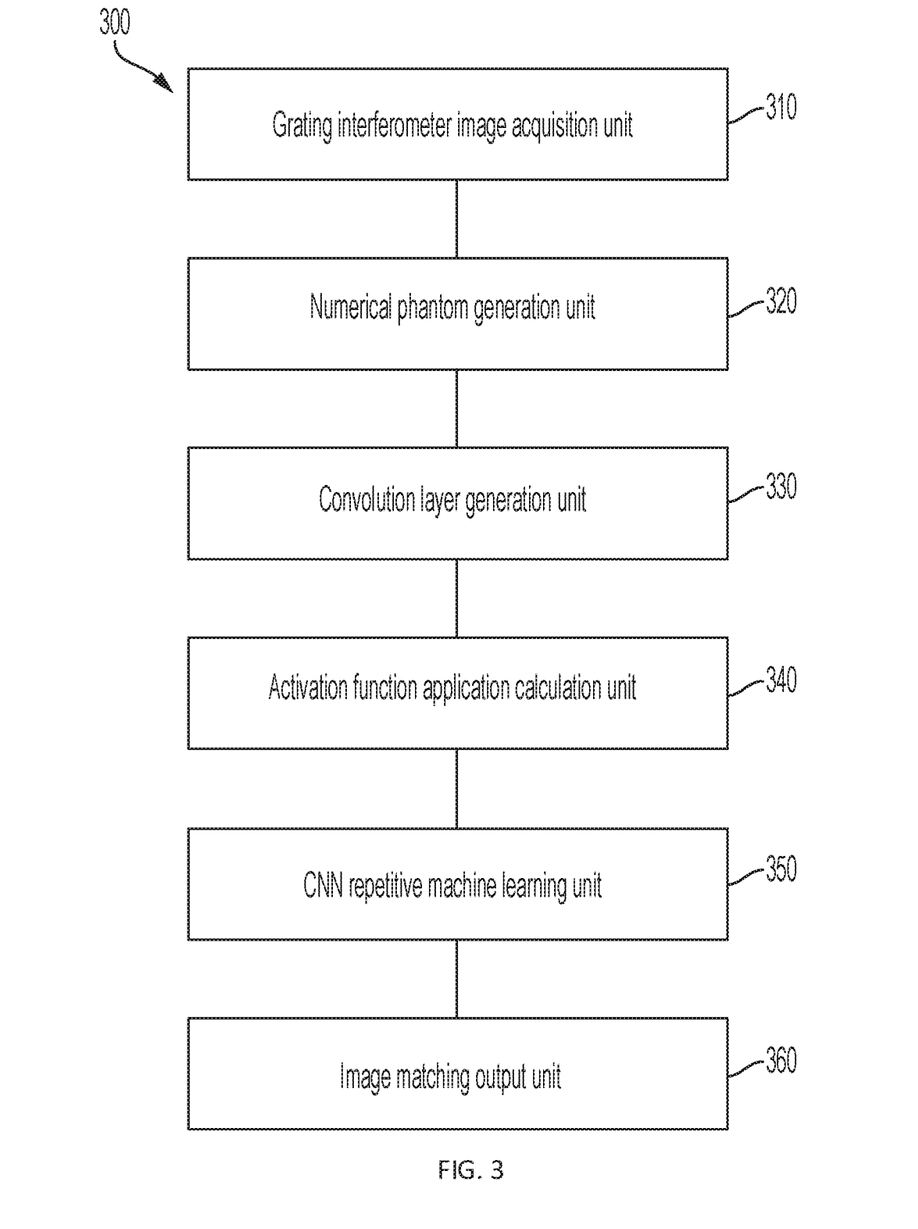
FIG. 3 illustrates a block diagram of a system for enhancing contrast sensitivity and resolution in a grating interferometer by machine learning, consistent with several embodiments of the present disclosure.

FIG. 3 illustrates a block diagram of a system 300 for enhancing contrast sensitivity and resolution in a grating interferometer by machine learning, consistent with several embodiments of the present disclosure. System 300 may include, in one embodiment, a grating interferometer image acquisition unit 310, a numerical phantom generation unit 320, a convolution layer generation unit 330, an activation function application calculation unit 340, a CNN repetitive machine learning unit 350 and an image matching output unit 360.

The grating interferometer image acquisition unit 310 is configured to acquire a relatively high resolution image and a relatively high sensitivity image by linearly moving the position of a sample from the symmetrical grating interferometer. The numerical phantom generation unit 320 is configured to generate a numerical phantom for performing machine learning. The convolution layer generation unit 330 is configured to perform calculation processing of a convolutional neural network to extract features from input data. The activation function application calculation unit 340 is configured to apply a ReLu (Rectified linear unit) activation function to an output value of the convolution calculation to perform smooth repetitive machine learning. The CNN repetitive machine learning unit 350 is configured to correct a convolution calculation factor while repeatedly performing forward propagation and backward propagation processes. The image matching output unit 360 is configured to match and provide as output features extracted by repetitive machine learning of the CNN repetitive machine learning unit.

The grating interferometer image acquisition unit 310 may be configured to acquire a pair images including a high contrast sensitivity image and high-resolution image of a sample from a symmetrical grating interferometer, linearly moving the position of sample relative to the gratings. The grating interferometer image acquisition unit 310 may be further configured to perform an image size rearrangement process to match different magnifications of the respective images.

The numerical phantomgeneration unit 320 is configured to measure the resolution, contrast sensitivity and noise of the acquired phase difference image, implement the same level of images in numerical simulation and generate a plurality of numerical phantoms for relatively high accuracy.

The convolution layer generation unit 330 is configured to generate a filter which is a convolution calculation factor in order to subject the input data to convolution, has a horizontal and vertical size smaller than the input data and allows the number of filters to be 32 or more.

In the convolution calculation of the input data and the filter in the convolution layer generation unit 330, zero padding, stride, and the size of generated filter are set in order to keep the result of the convolution calculation equal to the horizontal and vertical size of the input image. The size of the output data corresponds to:

$$(C_o, R_o) = \left( \frac{C_i + 2P - C_f}{S} + 1, \frac{R_i + 2P - R_f}{S} + 1 \right) \quad (1)$$

where $(C_o, R_o)$ is the size of the output data (C=column, R=row), $(C_i, R_i)$ is the size of the input data, S is the stride, P is zero-padding, and $(C_f, R_f)$ is the size of the filter.

In the convolution calculation of the input data and the filter in the convolution layer generation unit 330, zero padding is performed to solve the problem that the edge information of the input data disappears, and the result of the convolution calculation adjusts the size of the output data to the same size as the input value by setting the stride to 1 (stride:=1) when the filter moves within the input data.

The activation function application calculation unit 340 is configured to apply a ReLu function to an output value obtained from the calculation of each convolution layer, thereby reducing an error that may occur during repetitive machine learning performed later.

In the CNN repetitive machine learning unit 350, the forward propagation uses the convolutional calculation of the input data generated by the simulation and the convolution calculation factor, and calculates a loss value of a cost function. The back propagation corrects weight and bias by partially differentiating the convolution calculation factor in the reverse direction of the forward propagation calculation in order to minimize the loss.

Figure 4:
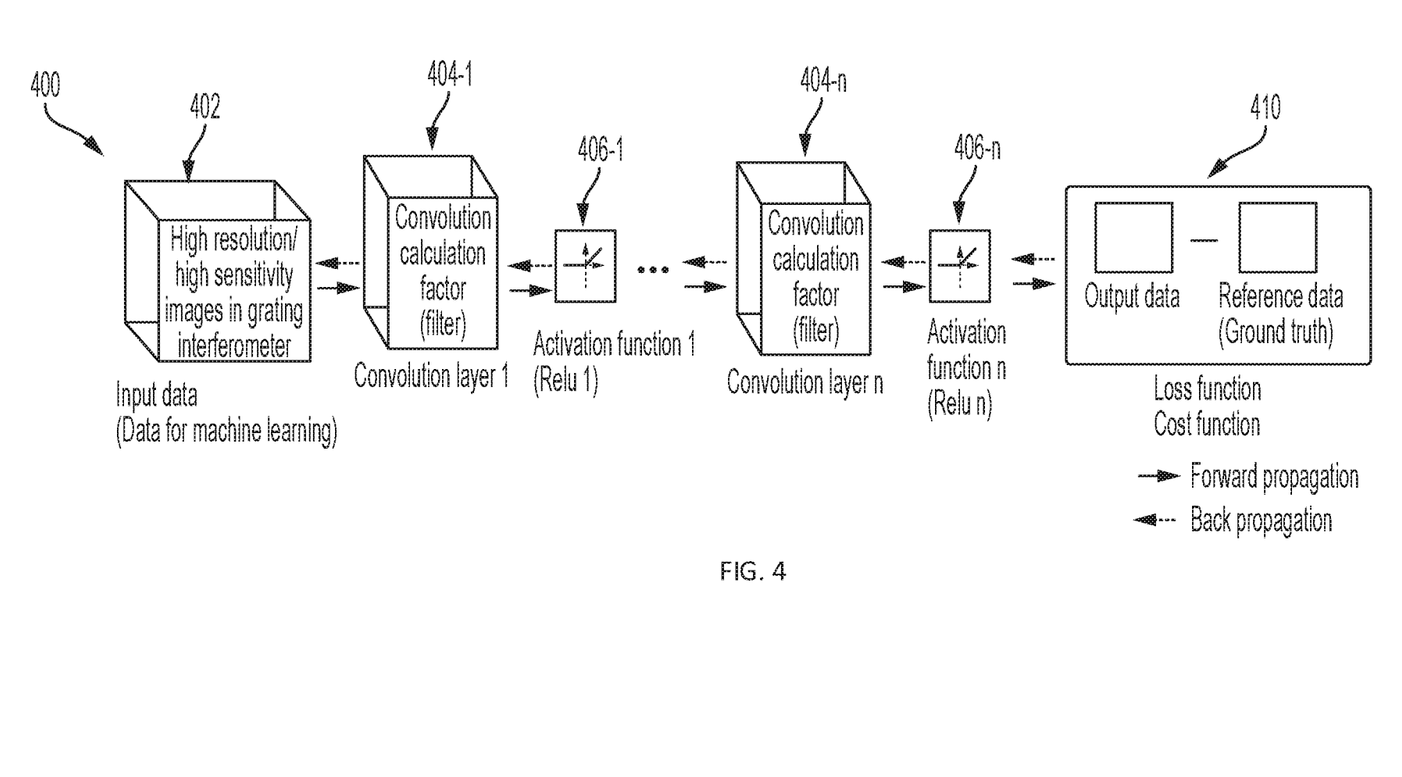
FIG. 4 is one example operational diagram illustrating machine learning (of a convolutional neural network (CNN)), consistent with several embodiments of the present disclosure.

The CNN repetitive machine learning unit 350 is configured to generate a cost function that reduces a difference between the result value of the convolution calculation performed from the input image through the mean square method 410, and the ground truth, and repeatedly performs forward propagation and backward propagation processes in a direction in which the generated cost function is reduced.

A method, apparatus and/or system for enhancing contrast sensitivity and resolution in a grating interferometer by machine learning according to the present disclosure has the following effects.

First, it is possible to improve both image contrast sensitivity and spatial resolution in a grating interferometer by machine learning.

Second, it is possible to extract image information having relatively high contrast sensitivity and relatively high resolution into images at various positions of a sample in a grating interferometer by using a convolutional neural network (CNN).

Third, it is possible to improve the contrast sensitivity and resolution of the phase difference image by using a convolutional neural network and thus provide a relatively high-quality medical image.

Fourth, it is possible to improve the contrast sensitivity and resolution of the phase difference image using a convolutional neural network, thereby increasing the applicability to other medical imaging systems beyond the X-ray and neutron imaging field, and developing new medical device market.

An apparatus, method and/or system for enhancing contrast sensitivity and resolution in a grating interferometer by machine learning according to the present disclosure may be configured to acquire both relatively high contrast sensitivity image and relatively high resolution image from a symmetric grating interferometer as shown in FIG. 2, and to improve both reduced contrast sensitivity and resolution through machine learning.

Machine learning is a technique that, when provided a learning model, derives an answer by integrating the features of an image based on the data accumulated by the computer. In other words, in one embodiment, machine learning, as used herein, corresponds to supervised learning.

A convolutional neural network (CNN), a type of artificial neural networks among a plurality of machine learning techniques, may be applied, but in the instant disclosure is not limited thereto. In other words, CNN is one nonlimiting example of an artificial neural network and this disclosure is not limited in this regard. CNN has been studied in various fields of image processing and computer vision, including, but not limited to, understanding images, extracting high-level abstracted information therefrom, or drawing pictures with new textures. Based on the ability to extract abstract formation in this way, it is possible to extract image information having relatively high contrast sensitivity and relatively high resolution into images at various positions of a subject in a grating interferometer system.

Turning again to FIG. 3, the operation mechanism of the convolutional neural network as applied herein is shown in FIG. 3.

The input data used for machine learning may be arranged in the form of a three-dimensional matrix (the width of the image, the length of the image, the number of images for each subject position). Such a three-dimensional matrix is configured to perform a convolution calculation with a convolution calculation factor (filter) and then apply a ReLU (Rectified linear unit) function to extract the non-linear relationship of the calculation result value.

In the process of convolution calculation, the depth is set to 1 while extracting all high-contrast sensitivity and high-resolution information by integrating three-dimensional values corresponding to the number of images for each subject position. The convolution layer is generated in a direction in which the horizontal and vertical sizes of the image are kept constant.

When a repetitive convolution calculation is performed in the convolution layer by using numerical phantoms implemented in simulation as the input data, a convolutional neural network is generated.

The convolutional neural network generated by repetitive machine learning extracts features of the phase difference image for each sample position acquired from the grating interferometer and generates a result image having high contrast sensitivity and high resolution.

As shown in FIG. 3, the apparatus, method and/or system for enhancing contrast sensitivity and resolution in a grating interferometer by machine learning includes: a grating interferometer image acquisition unit 310 that acquires images for each position of a sample from the grating interferometer, a numerical phantom generation unit 320 that additionally generates a numerical phantom similar to actual experimental images by simulation, a convolution layer generation unit 330 for constructing a convolutional neural network, an activation function application calculation unit 340 that applies a ReLu (Rectified linear unit) activation function to the convolution calculation result to perform efficient smooth repetitive machine learning, a CNN repetitive machine learning unit 350 that completes the convolutional neural network by repeatedly performing forward propagation and backward propagation processes on the generated convolution layer and activation function application unit, and an image matching output unit 360 that matches and outputs features extracted by repetitive machine learning of the CNN repetitive machine learning unit 350.

Here, the forward propagation constructs a convolutional neural network in a direction in which the size of the input image generated by the numerical simulation is maintained, and performs a convolution calculation. The forward propagation is a process for calculating the loss value after the result values generated through several convolution calculations are compared with the reference value (ground-truth) using the mean square error method.

And, the back propagation corrects weight and bias, which are the convolution factors, by performing the calculation in the reverse direction in order to reduce the calculated error values. The ideal weight and bias can be inferred by repeatedly performing forward propagation and back propagation processes several times.

In the apparatus for enhancing contrast sensitivity and resolution in a grating interferometer by machine learning according to the present disclosure having such a configuration, techniques for deriving relatively high contrast sensitivity and relatively high resolution images by applying machine learning algorithms to the X-ray grating interferometer will be described for each operation in detail below.

Figure 5:
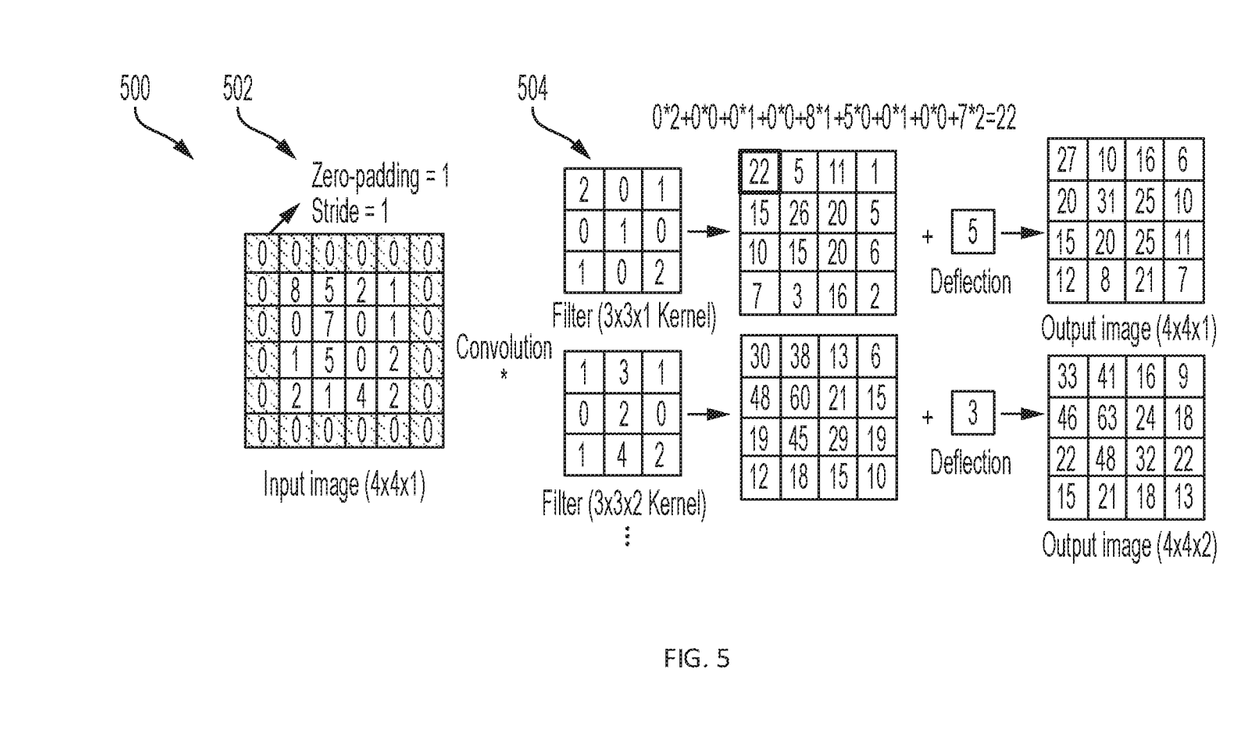
FIG. 5 illustrates one example convolution calculation process, consistent with the present disclosure.

FIG. 4 is one example operational diagram 400 illustrating machine learning (of a convolutional neural network (CNN)), consistent with several embodiments of the present disclosure. FIG. 5 illustrates one example convolution calculation process 500, consistent with the present disclosure. FIGS. 4 and 5 may be best understood when considered in combination with FIG. 3.

The grating interferometer image acquisition unit 310 is configured to acquire input images 402, 502 including a relatively high resolution and relatively low sensitivity image in which a position of a sample is located close to a detector from a symmetrical grating interferometer and a relatively high contrast sensitivity and relatively low resolution images in which a position of a sample is located close to a phase grating G1.

The numerical phantom generation unit 320 is configured to measure contrast sensitivity, image noise, and resolution information of the respective images from the acquired images and implement such information by numerical simulation including the process of producing images by contrast sensitivity and resolution and reference images (samples that include shape information and sensitivity information of the subject, ground-truth). A relatively large number, e.g., on the order of tens of thousands, of various types of samples may be generated for relatively more accurate machine learning.

The convolution layer generation unit 330 is configured to generate a plurality of filters 504 in order to subject the input data to convolution, and the horizontal and vertical sizes of the filter generated in one convolution layer, e.g., convolution layers 404-1, . . . , 404-n, are set to be smaller than the input data and the number of filters is set to be 32 or more. The number of the convolution layers generated is set to be three or more. The greater the number of the convolution layers generated, the higher the accuracy of machine learning.

FIG. 5 schematically illustrates the process 500 of convolution calculation of an input data 502 and a filter 504. In general, the calculation processing of the convolutional neural network reduces the size of the input data. Therefore, when zero padding in FIG. 5 is not performed, there may be a problem that the edge information of the input data disappears, and thus zero padding is performed. The convolution calculation is configured to adjust the size of the output data to the same size as the input value by setting the stride to 1 (stride=1) when the filter moves within the input data.

The size of the output data can be calculated according to Equation (1), wherein $(C_o, R_o)$ is the size of the output data (C=column, R=row), $(C_i, R_i)$ is the size of the input data, S is the stride, P is zero-padding, and $(C_f, R_f)$ is the size of the fitter.

In the convolution calculation for image matching, the size of the input data is kept the same during the calculation process. Thus, appropriate zero padding, stride, and filter size are set through Equation (1).

The activation function application calculation unit 340 is configured to perform a ReLu (Rectified linear unit) activation function application calculation, e.g., ReLU 406-1, . . . , 406-n. When the result value of the convolution calculation is greater than 0 based on the definition of ReLu function, the result value is outputted as it is, and when it is smaller than 0, the result value is outputted as 0.

Figure 6A:
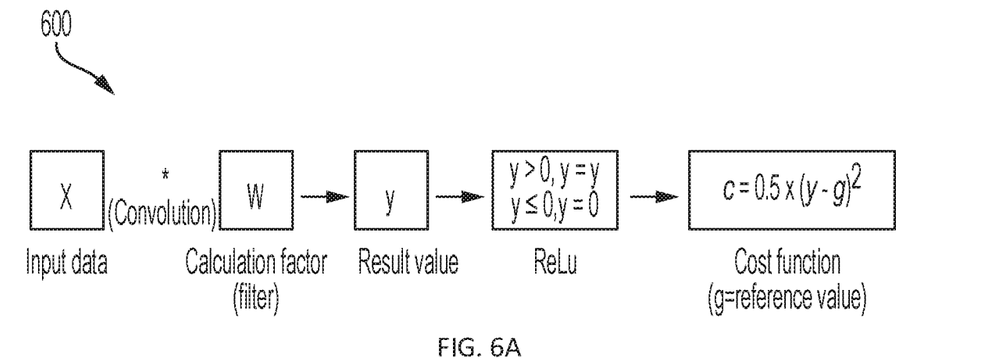
FIGS. 6A and 6B illustrate example operations of forward propagation and backward propagation for machine learning, consistent with several embodiments of the present disclosure.
Figure 6B:
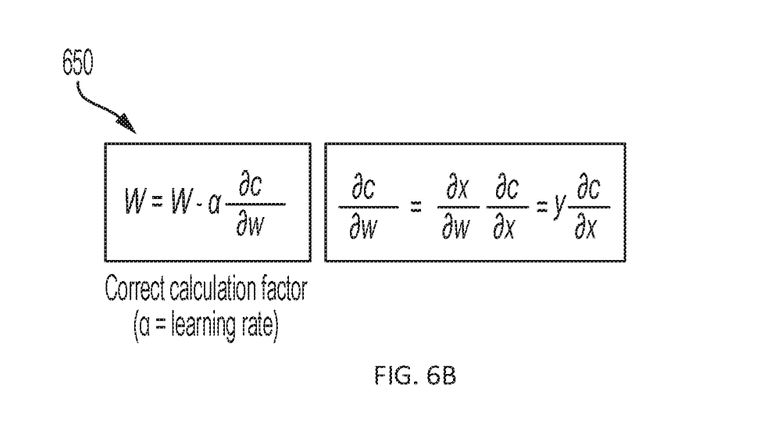

FIGS. 6A and 6B illustrate example operations of forward propagation 600 and backward propagation 650 for machine learning, consistent with several embodiments of the present disclosure. FIG. 6A illustrates a forward propagation calculation formula for CNN repetitive machine learning and finally calculates a loss value c, i.e., cost function. FIG. 6B illustrates a backward propagation calculation formula for CNN repetitive machine learning and also illustrates a process of calculating a gradient by taking a partial differentiation to the forward propagation calculation formula in order to correct the weight which is a convolution calculation factor.

The CNN repetitive machine learning unit 350 is configured to minimize the loss value of the cost function calculated using the mean square error method through repetitive forward propagation and backward propagation calculation processes. Through the CNN repetitive machine learning unit 350, a CNN neural network capable of matching relatively high resolution and relatively high contrast sensitivity images in grating interferometer is constructed, and by applying an actual medical image acquired from the a grating interferometer image acquisition unit 310 to the CNN neural network, it is possible to acquire relatively high resolution and relatively high contrast sensitivity images to be finally obtained.

The method for enhancing contrast sensitivity and resolution in a grating interferometer by machine learning according to the present disclosure will be described in detail as follows.

Figure 7:
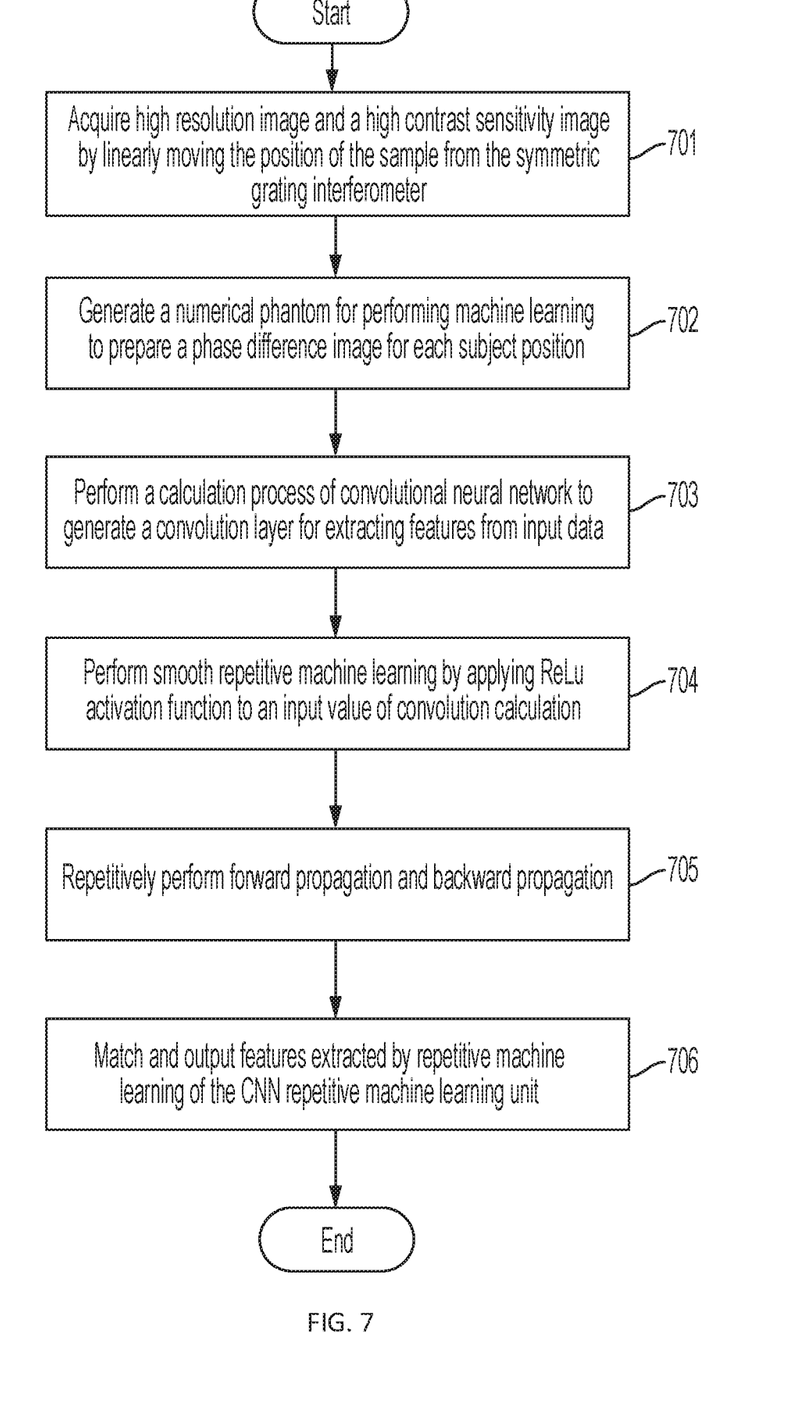
FIG. 7 is a flowchart illustrating enhancing contrast sensitivity and resolution in a grating interferometer by machine learning, consistent with several embodiments of the present disclosure.

FIG. 7 is a flowchart 700 illustrating enhancing contrast sensitivity and resolution in a grating interferometer by machine learning consistent with several embodiments of the present disclosure. The operations of flowchart 700 may be performed, for example, by a system for enhancing contrast sensitivity and resolution in a grating interferometer by machine learning 300 of FIG. 3 and/or according to machine learning process 400 of FIG. 4 and forward propagation 600 and backward propagation 650 for machine learning of FIGS. 6A and 6B. A relatively high-resolution image and a relatively high contrast sensitivity image are acquired by linearly moving the position of the sample from the symmetric grating interferometer at operation 701.

The resolution, sensitivity, and noise of the image are measured through the phase difference image acquired at operation 701, and a similar numerical phantom is generated through simulation at operation 702.

A convolution layer is generated by generating a filter composed of various weights and biases for convolution of the input data at operation 703.

The filter size, zero padding, and stride values are set appropriately so that the horizontal and vertical sizes of the input data are identically outputted during the convolution calculation process at operation 703.

Then, the ReLu function is applied to activate the value of the convolution calculation result of the input data at operation 704.

The forward propagation and backward propagation calculation processes are repeatedly performed through continuous arrangement of a plurality of convolution layers and ReLu activation functions to correct the weight and bias that are the convolution calculation factor at operation 705.

Subsequently, the convolutional neural network is completed by repeatedly performing the convolution calculation, and the phase difference image acquired in operation 701 is applied to the convolutional neural network, thereby finally outputting images with relatively high sensitivity and relatively high resolution at operation 706.

The apparatus and method for enhancing contrast sensitivity and resolution in a grating interferometer by machine learning according to the present disclosure as described herein include acquiring a relatively high contrast sensitivity image and a relatively high resolution image by linearly moving a sample from a symmetrical grating interferometer, and supplementing the resolution and contrast sensitivity degradation issues that arise from the image captured here by using a convolutional neural network (CNN).

Looking at the simulation results of the apparatus and method for enhancing contrast sensitivity and resolution in a grating interferometer by machine learning according to the present disclosure as described herein, it can be seen that the contrast sensitivity and resolution of the phase difference image can be improved by using a convolutional neural network to provide a high quality medical image.

Figure 8A:
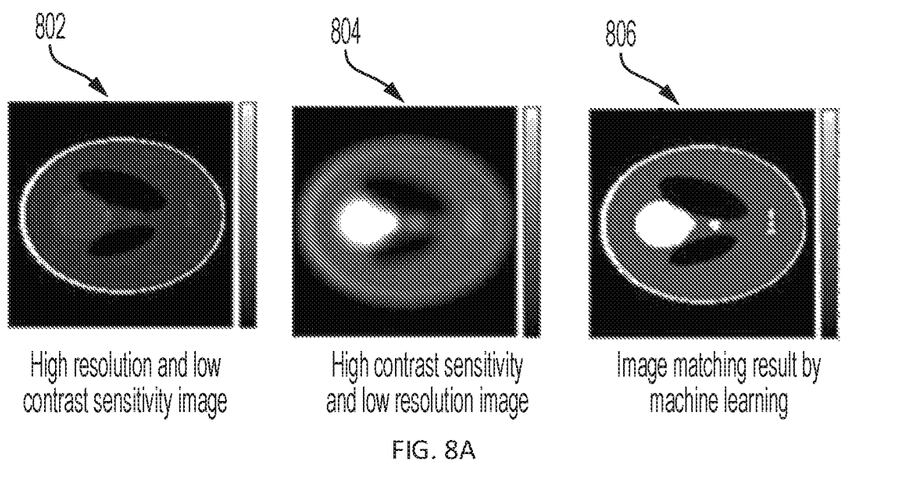
FIGS. 8A and 8B illustrate simulation results of phantom images, consistent with the present disclosure.
Figure 8B:
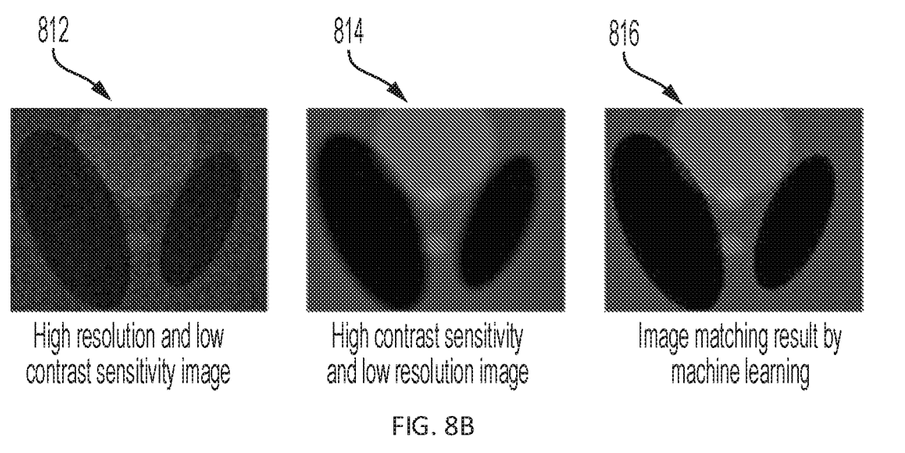

FIGS. 8A and 8B illustrate simulation results of phantom images, consistent with the present disclosure. Simulation results 802, 812 are relatively high resolution and relatively low contrast sensitivity images. Simulation results 804, 814 are relatively high contrast sensitivity and relatively low resolution images. Simulation results 806, 816 are relatively high resolution and relatively low contrast sensitivity images.

As described herein, it will be understood that the apparatus, method and/or system described herein may be implemented in a modified form without departing from the essential characteristics of the present disclosure.

Therefore, the described embodiments should be considered from an illustrative viewpoint rather than a limiting viewpoint. The scope of the disclosure is defined not in the above-mentioned description but in the claims, and all differences that fall within the equivalent scope should be construed as being included in the present disclosure.

What is claimed is:

1. An apparatus for enhancing contrast sensitivity and resolution in a grating interferometer by machine learning, the apparatus comprising:
    a grating interferometer image acquisition unit configured to acquire a first image with a target resolution and a second image with a target contrast sensitivity from a symmetrical grating interferometer by linearly moving a position of a sample in the interferometer;
    a numerical phantom generation unit configured to generate a numerical phantom for performing machine learning;
    a convolution layer generation unit configured to perform calculation processing of a convolutional neural network to extract features from input data;
    an activation function application calculation unit configured to apply a ReLu (Rectified linear unit) activation function to an output value of the convolution calculation to perform smooth repetitive machine learning;
    a CNN (convolutional neural network) repetitive machine learning unit configured to correct a convolution calculation factor while repeatedly performing forward propagation and backward propagation processes; and
    an image matching output unit configured to match and provide as output features extracted by repetitive machine learning of the CNN repetitive machine learning unit.

2. The apparatus for enhancing contrast sensitivity and resolution in a grating interferometer by machine learning according to claim 1, wherein
    the grating interferometer image acquisition unit is configured to acquire a pair of images including a first image with a target contrast sensitivity and a second image with a target resolution by installing a symmetrical grating interferometer and linearly moving the position of the sample and to perform an image size rearrangement process to match different magnifications of the respective images.

3. The apparatus for enhancing contrast sensitivity and resolution in a grating interferometer by machine learning according to claim 1, wherein
the numerical phantom generation unit is configured to measure the resolution, contrast sensitivity and image noise of the acquired images, implement the measured resolution, contrast sensitivity, and image noise in numerical simulation and generate a plurality of numerical phantoms.

4. The apparatus for enhancing contrast sensitivity and resolution in a grating interferometer by machine learning according to claim 1, wherein
the convolution layer generation unit is configured to generate a filter for each convolution layer which is a convolution calculation factor in order to subject the input data at each layer to convolution, has a horizontal and vertical size smaller than the input data, and allows the number of filters to be 32 or more.

5. The apparatus for enhancing contrast sensitivity and resolution in a grating interferometer by machine learning according to claim 4, wherein
the convolution calculation of the input data and the filter in the convolution layer generation unit comprises setting zero padding, stride, and the size of the generated filter in order to keep the result of the convolution calculation equal to a horizontal and vertical size of at least one of the first and second images,
the size of the output data comprises $$(C_o, R_o) = \left(\frac{C_i + 2P - C_f}{S} + 1, \frac{R_i + 2P - R_f}{S} + 1\right),$$

where $(C_o, R_o)$ is the size of the output data (C=column, R=row), $(C_i, R_i)$ is the size of the input data, S is the stride, P is zero-padding, and $(C_f, R_f)$ is the size of the filter.

6. The apparatus for enhancing contrast sensitivity and resolution in a grating interferometer by machine learning according to claim 5, wherein
in the convolution calculation of the input data and the filter in the convolution layer generation unit,
zero padding is performed, and
the result of the convolution calculation adjusts the size of the output data to the same size as the input value by setting the stride to 1 (stride=1) when the filter is moved within the input data.

7. The apparatus for enhancing contrast sensitivity and resolution in a grating interferometer by machine learning according to claim 1, wherein
the activation function application calculation unit is configured to apply a ReLu function to an output value obtained from the calculation of each convolution layer, thereby reducing an error that may occur during repetitive machine learning performed later.

8. The apparatus for enhancing contrast sensitivity and resolution in a grating interferometer by machine learning according to claim 1, wherein
in the CNN repetitive machine learning unit,
the forward propagation uses the convolutional calculation of the input data generated by the simulation and the convolution calculation factor to finally calculate a loss value of a cost function, and
the back propagation corrects weight and bias by partially differentiating the convolution calculation factor in the reverse direction of the forward propagation calculation in order to minimize the loss value.

9. The apparatus for enhancing contrast sensitivity and resolution in a grating interferometer by machine learning according to claim 1, wherein
the CNN repetitive machine learning unit is configured to generate a cost function that reduces the difference between a result value of the convolution calculation performed from an input image and a ground truth image, and
repeatedly perform forward propagation and backward propagation processes in a direction in which the generated cost function is reduced.

* * * * *